United States Patent
Kirakossian et al.

(10) Patent No.: US 11,266,988 B2
(45) Date of Patent: Mar. 8, 2022

(54) SMALL VOLUME SELF-METERED BLOOD SEPARATION DEVICE

(71) Applicant: Wainamics, Inc., Pleasanton, CA (US)

(72) Inventors: Hrair Kirakossian, San Jose, CA (US); Ming Tan, Santa Cruz, CA (US)

(73) Assignee: Wainamics, Inc.

( * ) Notice: Subject to any disclaimer, the term of this patent is extended or adjusted under 35 U.S.C. 154(b) by 82 days.

(21) Appl. No.: 16/491,295

(22) PCT Filed: Mar. 14, 2018

(86) PCT No.: PCT/US2018/022329
§ 371 (c)(1),
(2) Date: Sep. 5, 2019

(87) PCT Pub. No.: WO2018/175169
PCT Pub. Date: Sep. 27, 2018

(65) Prior Publication Data
US 2020/0030792 A1    Jan. 30, 2020

Related U.S. Application Data

(60) Provisional application No. 62/473,946, filed on Mar. 20, 2017.

(51) Int. Cl.
*B01L 3/00* (2006.01)
(52) U.S. Cl.
CPC ....... *B01L 3/50273* (2013.01); *B01L 2300/12* (2013.01); *B01L 2400/0406* (2013.01); *B01L 2400/0481* (2013.01)

(58) Field of Classification Search
None
See application file for complete search history.

(56) References Cited

U.S. PATENT DOCUMENTS

| 4,477,575 A | 10/1984 | Vogel |
| 4,933,092 A | 6/1990 | Aunet |

(Continued)

FOREIGN PATENT DOCUMENTS

| WO | WO2010/111086 | 9/2010 |
| WO | WO2014/172234 | 10/2014 |

(Continued)

OTHER PUBLICATIONS

Becker et al, "Highly efficient on-chip plasma/serum generation for disposable point-of-care devices," 14th International Conference on Miniaturized Systems for Chemistry and Life Sciences, Groningen, The Netherlands (Oct. 3-7, 2010).

(Continued)

*Primary Examiner* — Dennis White
*Assistant Examiner* — Bryan Kilpatrick
(74) *Attorney, Agent, or Firm* — Stephen C. Macevicz

(57) ABSTRACT

The invention, is directed to devices and methods for low cost and convenient separation, of plasma from whole blood. In some embodiments, devices of the invention comprise an integrated collection of channels and chambers m a body that permit acquisition of a blood sample by capillary action, centrifugal separation of cells from plasma, and manual dispensing of purified plasma by simple pinching of a bellows chamber to force air into plasma-holding channels which thereby expels a predetermined volume of the purified plasma.

21 Claims, 9 Drawing Sheets

(56) References Cited

U.S. PATENT DOCUMENTS

| | | |
|---|---|---|
| 4,987,085 A | 1/1991 | Allen |
| 5,110,724 A | 5/1992 | Hewett |
| 5,262,067 A | 11/1993 | Wilk |
| 5,728,306 A | 3/1998 | Breillatt |
| 5,766,552 A | 6/1998 | Doshi |
| 5,798,272 A | 8/1998 | Allen |
| 5,895,575 A | 4/1999 | Kraus |
| 5,996,811 A | 12/1999 | Kitajima |
| 6,197,598 B1 | 3/2001 | Schrier |
| 7,159,474 B2 | 1/2007 | Arabian |
| 7,404,931 B2 | 7/2008 | Frey |
| 8,057,672 B2 | 11/2011 | Chung |
| 8,470,259 B2 | 6/2013 | Gupta |
| 8,889,071 B2 | 11/2014 | Aota |
| 8,999,161 B2 | 4/2015 | Mathias |
| 2003/0206828 A1 | 11/2003 | Bell |
| 2005/0101979 A1 | 5/2005 | Alden |
| 2005/0106066 A1* | 5/2005 | Saltsman ............. F04B 43/043 422/504 |
| 2006/0207937 A1 | 9/2006 | Bonaguidi |
| 2008/0128341 A1 | 6/2008 | Jang |
| 2009/0181411 A1* | 7/2009 | Battrell ............. B01L 3/502738 435/7.92 |
| 2010/0093551 A1 | 4/2010 | Montagu |
| 2012/0024788 A1 | 2/2012 | Kelso |
| 2014/0263059 A1 | 9/2014 | Burg |
| 2015/0125882 A1* | 5/2015 | Bornheimer ........ B01F 13/0059 435/7.24 |
| 2016/0109467 A1 | 4/2016 | Kolb et al. |
| 2017/0003270 A1 | 1/2017 | Beguin et al. |

FOREIGN PATENT DOCUMENTS

| | | |
|---|---|---|
| WO | WO2016/073415 | 5/2016 |
| WO | PCT/US2018/022329 | 5/2018 |
| WO | WO2018/175169 | 9/2018 |

OTHER PUBLICATIONS

Gong et al, "Field tested millimeter-scale blood filtration device for point-of-care applications," Biomicrofluidics, 7: 044111 (2013).

Haeberle et al, "Microfluidic platforms for lab-on-a-chip applications," LabChip, 7: 1094-1110 (2007).

Homsy et al, "Development and validation of a low cost blood filtration element separating plasma from undiluted whole blood," Biomicrofluidics, 6: 012804 (2012).

Moscovici et al, "Electrical power free, low dead volume, pressure-driven pumping for microfluidic applications," Biomicrofluidics, 4: 046501 (2010).

Toner et al, "Blood-on-a-chip," Annu. Rev. Biomed. Eng., 7:77-103 (2005).

* cited by examiner

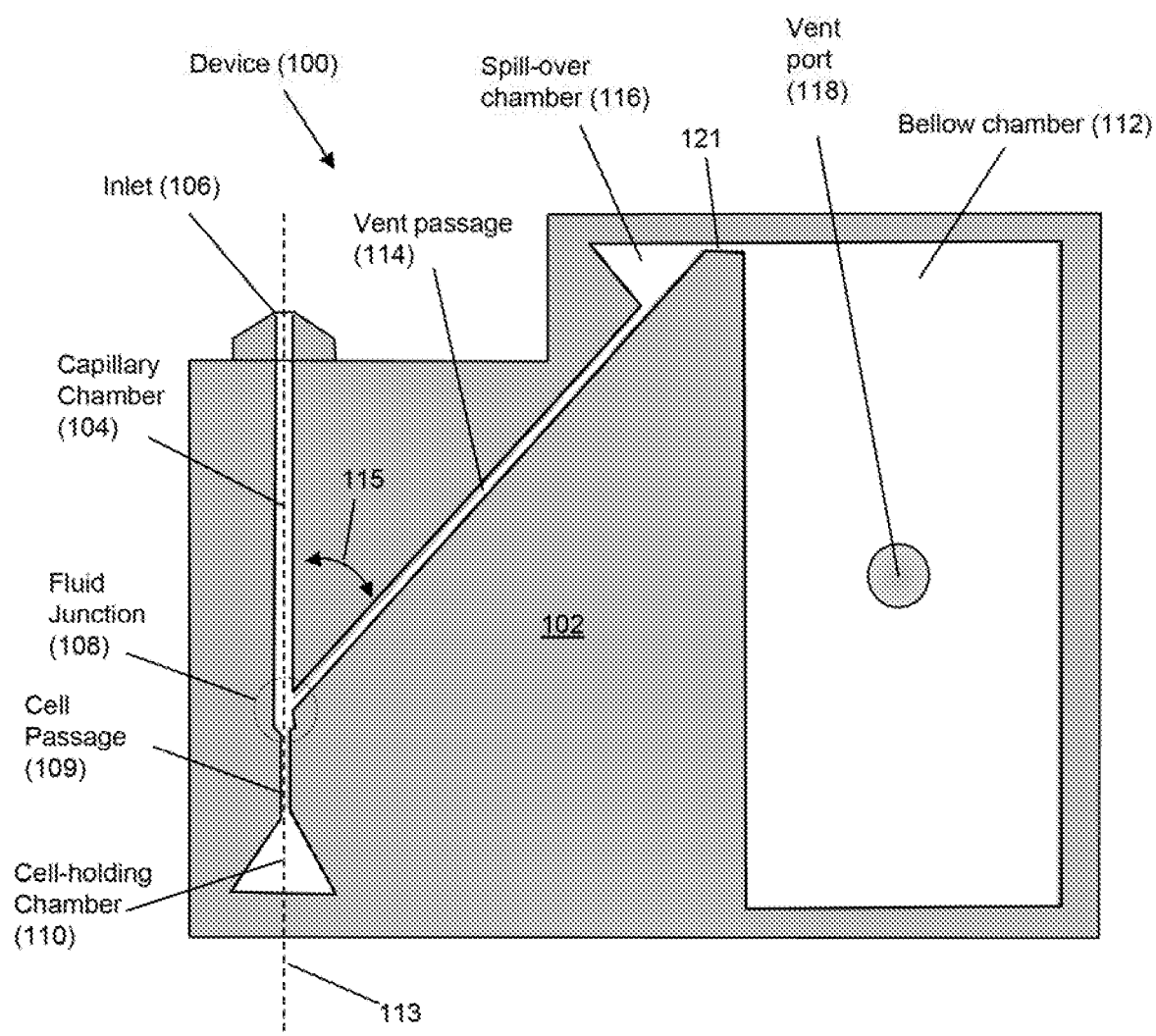
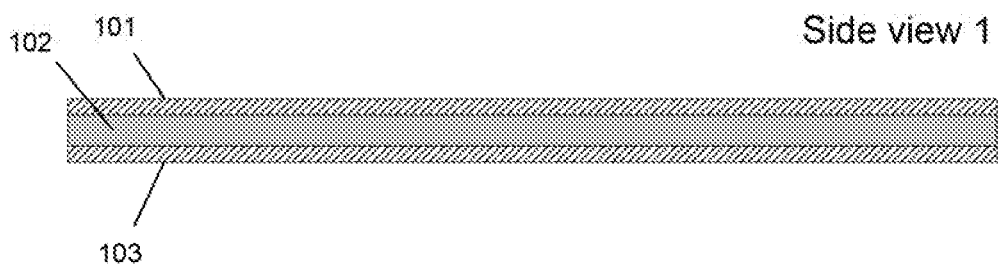
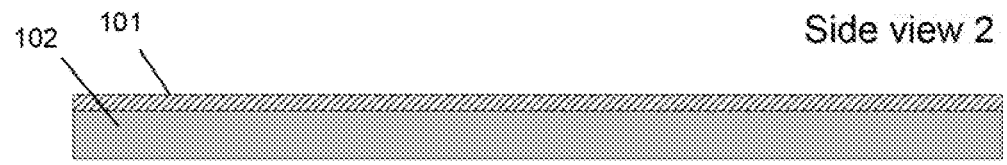
Fig. 1A

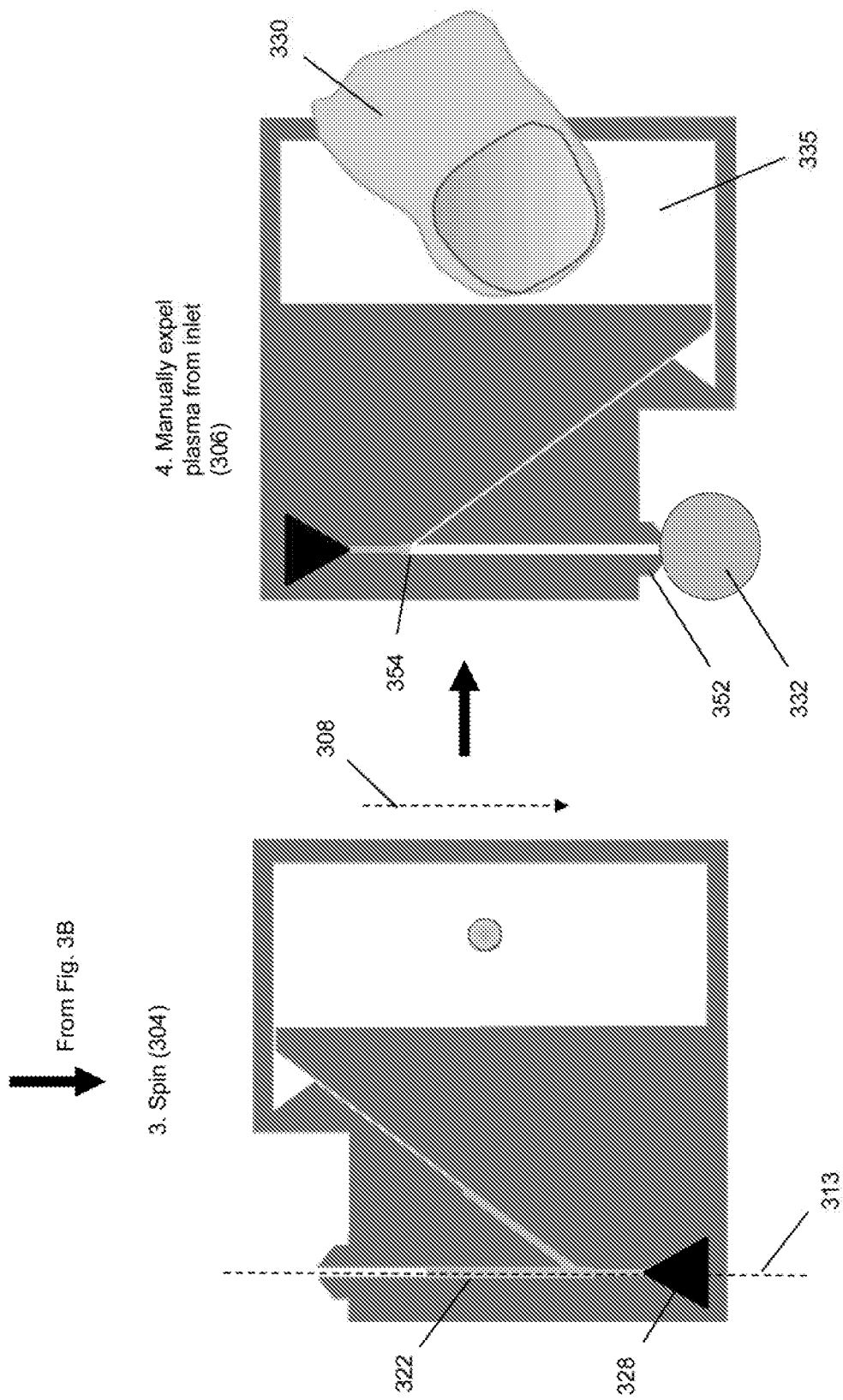

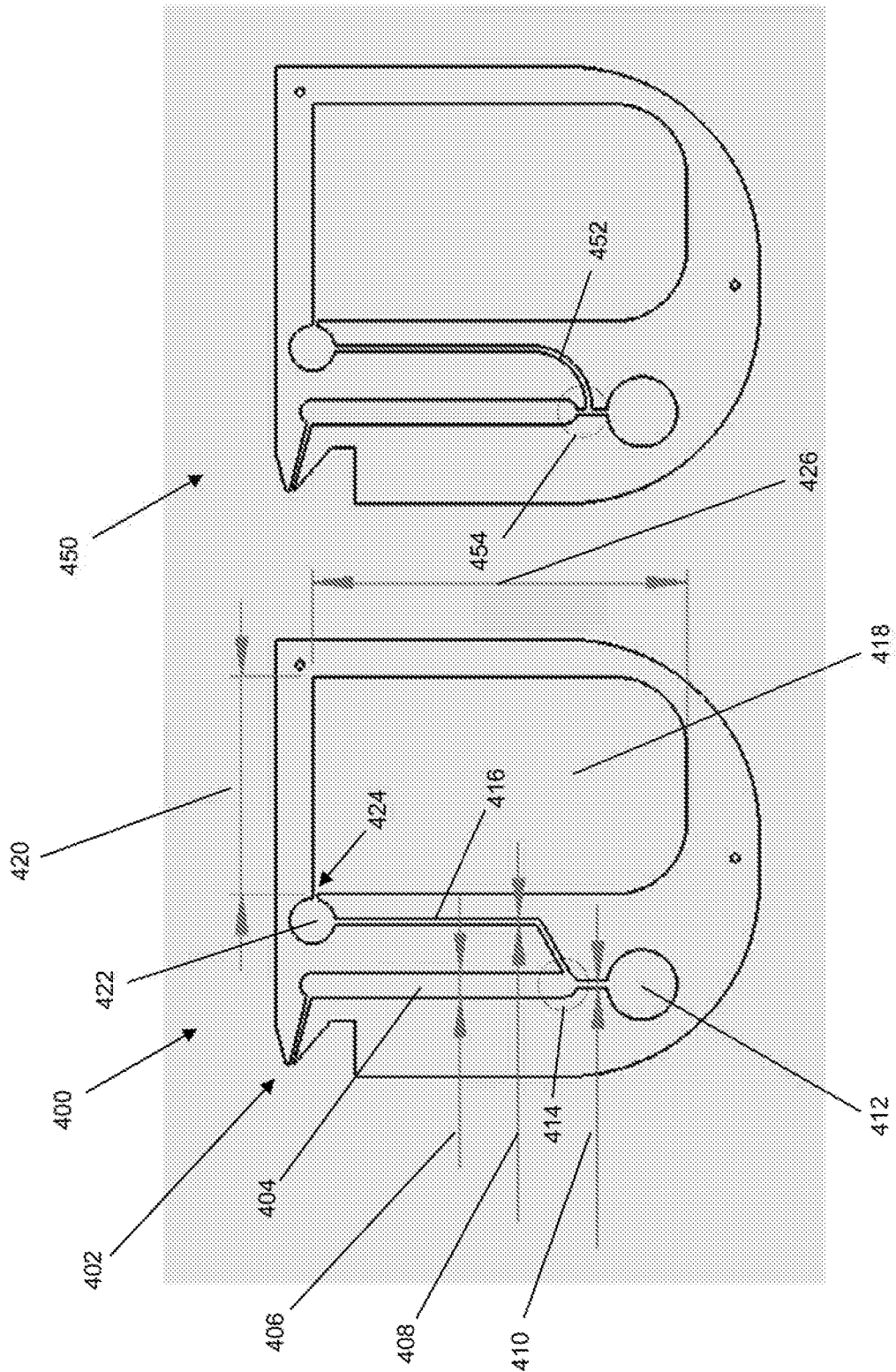

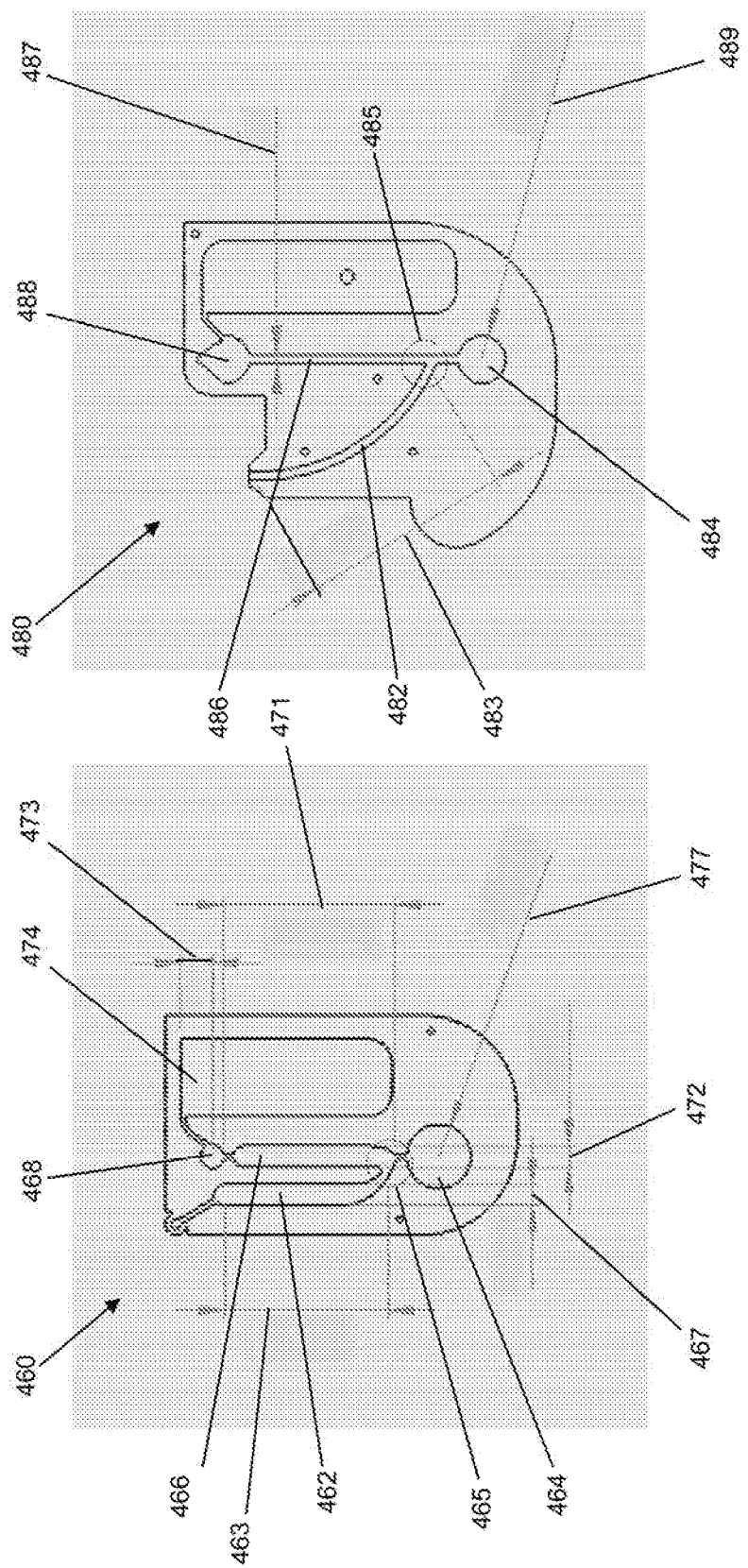

SMALL VOLUME SELF-METERED BLOOD SEPARATION DEVICE

This is application was filed under 35 USC 1.371(f) based on International Application serial number PCT/US2018/022329 filed 14 Mar. 2018, which claims priority from U.S. provisional application Ser. No. 62/473946 filed 20 Mar. 2017. Each of the foregoing applications is incorporated herein by reference in its entirety.

Many clinical tests and research assays require a sample of plasma, the liquid component of blood after cells have been removed. Most, if not all, techniques for obtaining plasma samples require some form of filtration and/or centrifugation. Each of these approaches has trade-offs: On one hand, filtration requires adsorbent and/or size selecting materials that may preferentially remove plasma constituents during separation; but on the other hand, filtration typically does not require specialized equipment to create conditions for separating blood cells from plasma; thus, filtration methods are especially attractive for use in resource-poor settings. Likewise, on one hand, centrifugation typically requires a laboratory setting with access to reliable power and specialized expertise; but on the other hand, centrifugation provides high quality plasma samples and efficient use of starting material.

It would be highly desirable, especially for medical applications in resource poor settings, if there were available techniques and devices for obtaining centrifugation-quality plasma samples without a need of a laboratory support infrastructure.

SUMMARY OF THE INVENTION

The invention is directed to methods and devices, including microfluidic devices, for rapid separation of plasma from small amounts of blood, such as obtainable from simple finger-prick blood-drawing techniques.

In some embodiments, the invention comprises a device for separating plasma from whole blood comprising the following elements: (a) a body comprising a capillary channel having a long axis and a predetermined channel volume and dimensions and having an inlet at a first end and a fluid junction at a second end; (b) a cell-holding chamber disposed opposite the fluid junction from the capillary channel in the body, the cell-holding chamber being in fluid communication with the fluid junction; (c) a bellows chamber disposed in the body, the bellows chamber providing a predetermined bellows volume enclosed by two substantially parallel walls wherein at least one wall contains a vent port there through and wherein at least one wall is pliant by manual action so that the predetermined bellows volume may be reduced by an amount substantially equal to the predetermined channel volume by manually pressing the two walls together; and (d) a vent passage disposed in the body, the vent passage providing fluid communication between the fluid junction and the bellows chamber, thereby providing fluid communication between the capillary channel and the bellows chamber; wherein the device is configured so that (i) the predetermined channel volume and dimensions allow the capillary channel to fill with blood by capillary action upon contact with a sample at the inlet, (ii) blood cells in the capillary channel sediment in the cell-holding chamber by centrifugation along the long axis of the capillary channel so that substantially only plasma remains in the capillary channel, and (iii) plasma in the capillary channel is expelled from the inlet by manually covering the vent port and pressing the walls of the bellows chamber together. In some embodiments, the vent passage is disposed in the body at a substantially acute angle with respect to the long axis of capillary channel so that cells in any excess blood from a sample that enters the vent passage are sedimented to the cell-holding chamber upon centrifugation.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the present invention.

BRIEF DESCRIPTION OF THE DRAWINGS

FIG. 1A illustrates a design of one embodiment of a device of the present invention showing the capillary channel configured so that its long axis is parallel with the direction of centrifugal force during operation.

FIGS. 3A-3D illustrate the operation of one embodiment of a device of the invention.

FIGS. 4A-4B and 4C-4D illustrate further embodiments of the present invention.

DETAILED DESCRIPTION OF THE INVENTION

Figure 1B:
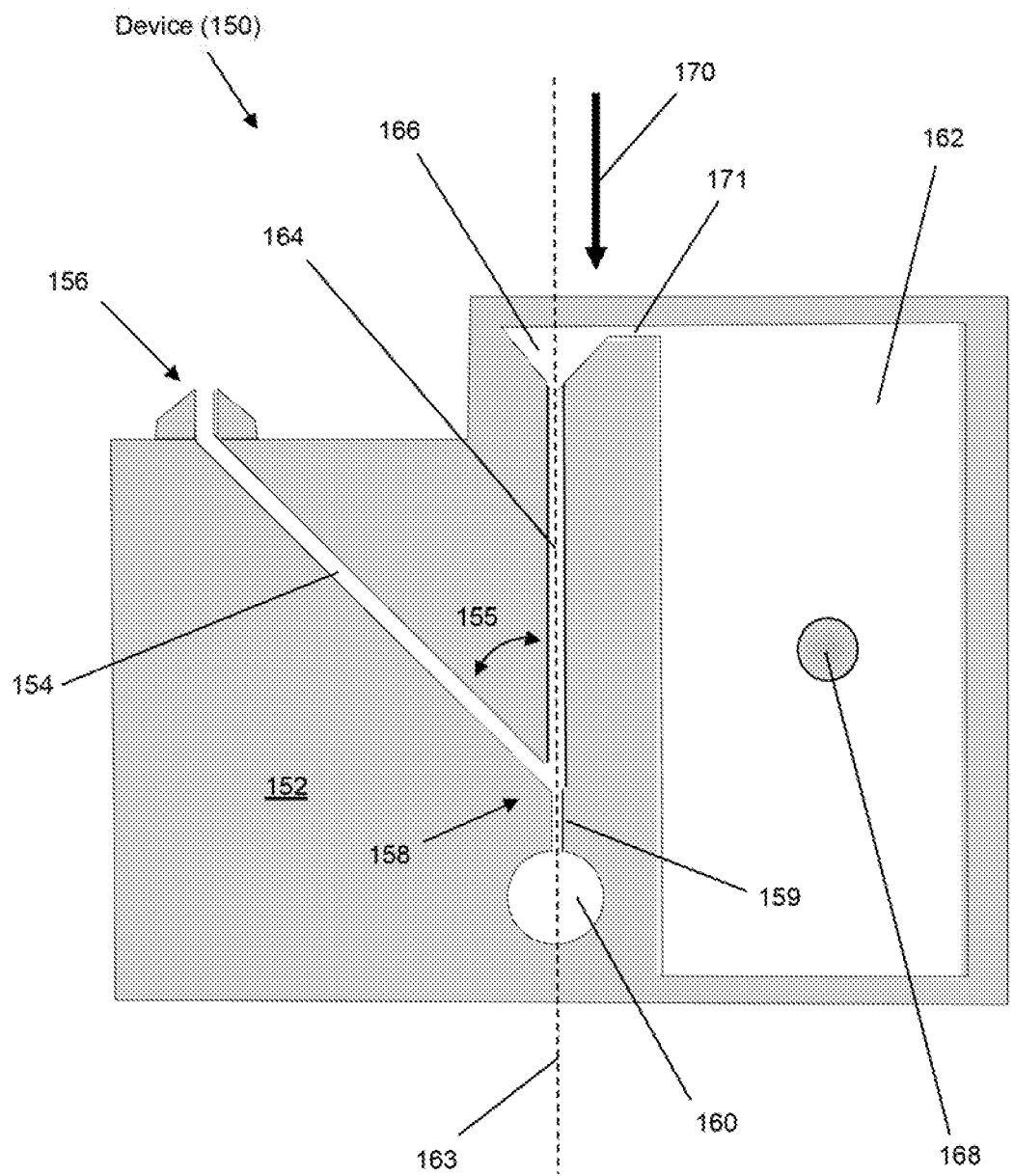
FIG. 1B illustrates a design of one embodiment of a device of the present invention showing the vent passage configured so that its long axis is parallel with the direction of centrifugal force during operation.

The general principles of the invention are disclosed in more detail herein particularly by way of examples, such as those shown in the drawings and described in detail. It should be understood, however, that the intention is not to limit the invention to the particular embodiments described. The invention is amenable to various modifications and alternative forms, specifics of which are shown for several embodiments. The intention is to cover all modifications, equivalents, and alternatives falling within the principles and scope of the invention.

The invention provides a low cost, efficient and disposable blood sampling device which extracts a plasma sample from a small amount of whole blood. In one aspect, devices of the invention employ capillary action to draw blood into the device, separate blood cells from plasma by centrifugation by spinning the device, and deliver a plasma sample by manually compressing a chamber that pneumatically drives the plasma, free of cells, out of the device. In some embodiments, devices of the invention separate red blood cells (RBCs) from plasma. In other embodiments, devices of the invention separate all blood cells from plasma. Exemplary devices (100) and (150) of the invention are shown schematically in FIGS. 1A and 1B.

In FIG. 1A, disposed in a linear order within body (102) are inlet (106), capillary channel (104), fluid junction (108), optional cell passage (109), and cell-holding chamber (110), wherein the long axis of capillary channel (104) is substantially collinear with this ordering. Inlet (106) and capillary channel (104) are in fluid communication with fluid junction (108) and cell-holding chamber (110). Cell passage (109) is optional in the sense that it could be fabricated as a passage or simply an opening connecting fluid junction (108) with cell-holding chamber (110). In some embodiments, inlet (106) may be disposed within a protrusion of body (102) to facilitate drawing a blood sample (for example, from a droplet) by capillary action. In some embodiments, inlet (106) may have a height from base to tip of about 2 mm. Inlet (106) may be collinear with capillary channel (104) or it may be at an angle, for example, to allow convenient contact with a blood droplet. In some embodiments, capillary channel (104) has a length of about 25 mm and a cross-sectional area of about 1 mm×1 mm, but one with ordinary skill in the art would understand that these dimensions may vary widely consistent with loading blood by capillary action. In some embodiments, cell passage (109) has a cross-sectional area of about 0.2 mm×1 mm and a length of about 5 mm, but again a skilled artisan would understand that these dimensions may vary widely and may be determined empirically for particular embodiments. In some embodiments, the length and cross-sectional dimensions of cell passage (109) are selected to substantially inhibit passage of red blood cells unless under the influence of centrifugal force. With such configurations, after sedimentation of RBCs into cell-holding chamber (110), RBCs are substantially prevented from moving back into fluid junction (108) or capillary channel (104) after a centrifugation step.

In normal operation, if the volume of blood entering the device is larger than the volume of the capillary channel, the excess volume of blood preferentially flows into the vent chamber instead of the cell passage in part because of the cross-sectional area of the cell passage is less than those of the capillary channel and the vent passage and, in part, because of the air-tightness of the cell-holding chamber. The latter feature ensures that a column of blood entering the device bypasses the cell passage and enters the vent passage because air in the vent passage can be pushed out of the device through the vent port, whereas the volume of air in the cell-holding chamber has nowhere to go, and can only be displace by exiting through the cell passage. The former feature ensures that fluid entering the cell passage (with a smaller cross sectional area than the vent passage) will have a smaller meniscus which is more resistant to being displaced by air in the cell-holding chamber, especially in the absence of a centrifugal force. On the other hand, the dominant forces on the blood changes when a centrifugal force is applied. That is, with application of a large enough centrifugal force, the lower density air will exchange places wall the higher density blood components in the cell-holding chamber. Thus, in some embodiments, the cell-holding chamber and cell passage are air-tight and the cell passage is dimensioned so that there is minimal likelihood, or it is impossible, for air from the cell-holding chamber to exchange with, or be displaced by, in-coming blood by capillary action alone. That is, in some embodiments, the cell-holding chamber and cell passage are air-tight and the cell passage is dimensioned so that there is minimal likelihood, or it is impossible, for air from the cell-holding chamber to exchange with, or be displaced by, blood entering the device absent the application of a centrifugal force. For particular embodiments, the cross-sectional area and length of the cell passage may be determined empirically. In some embodiments, a magnitude of centrifugal force is applied that provides sedimentation of ninety-nine percent of red blood cells within a period of from 1 to 5 minutes. In other embodiments, a magnitude of centrifugal force is applied that provides sedimentation of ninety-nine percent of red blood cells within a period of from 1 to 2 minutes. In other embodiments, a magnitude of centrifugal force is applied that provides sedimentation of ninety-five percent of red blood cells within a period of from 1 to 2 minutes. In some embodiments, a cross-sectional area of the cell passage is selected that is less than the cross-sectional area of the vent passage. In some embodiments, a cross-sectional area of the cell passage is selected that is, less than the cross-sectional area of the vent passage, and less than the cross-sectional area of the capillary channel. In some embodiments, a cross-sectional area of the cell passage is equal to or less than seventy-five percent the cross-sectional area of the vent passage. In some embodiments, a cross-sectional area of the cell passage is equal to or less than fifty percent the cross-sectional area of the vent passage.

Also disposed in body (102) are bellows chamber (112), vent passage (114) and optionally spill-over chamber (116), which is disposed between vent passage (114 and bellows chamber (112). In sonic embodiments, vent passage (114) is connected to fluid junction (108) at acute angle (115) with respect to axis (113) of capillary channel (104) and provides fluid communication between fluid function (108) and bellows chamber (112). The design of vent passage (114) may vary widely; for example, its geometry may be linear or curvilinear and its cross-sectional area may vary widely consistent with loading of blood by capillary action. A design is selected that permits blood cells therein to be readily moved to cell-holding chamber (110) under centrifugation. Acute angle (115) is selected so that cells that may enter vent passage (114) may be readily relocated by spinning or centrifugation to cell-holding chamber (110). Generally, fluid junction (108) is disposed in body (102) in a location in the direction of a centrifugal force (when applied) with respect to the end of vent passage (114) connected to bellows chamber (112) and/or spill-over chamber (116). (That is, fluid junction (108) is below vent passage (114), as illustrated in FIG. 1A). In some embodiments, acute angle (115) is in the range of from 0 to 45 degrees.

In FIG. 1B, another embodiment (150) is illustrated in which cell-holding chamber (160), cell passage (159), fluid junction (158), vent passage (164) and spill-over chamber (166) are arranged in body (152) substantially linearly along axis (163) (the long axis of vent passage (164)) in the recited order, wherein such linear ordering is substantially parallel to the direction of an applied centrifugal force during operation. This configuration ensures that air from cell holding chamber (160) will evacuate preferentially to spill-over chamber (166) during operation and not to inlet (156). In other respects, embodiment (150) of FIG. 1B is similar to that of FIG. 1A. Namely, blood is drawn into capillary passage (154) (and possibly into vent passage (164)) through inlet (156) by capillary action. A centrifugal force (170) is applied in a direction parallel to axis (163) described above so that cells, e.g. red blood cells, are sedimented through cell passage (159) into cell-holding chamber (160), thereby leaving cell-free plasma in capillary channel 154) and possibly vent passage (164). Such centrifugal force may be applied by, centrifugation of device (150), which may be carried out using a holder adapted for use in a commercial centrifuge or a special purpose centrifuge made specifically for device (150). As with the embodiment of FIG. 1A, a volume of cell-free plasma may be expelled from inlet (156) by manually compressing bellows chamber (162) with either finger or thumb placed over vent port (168), thereby forcing a volume of air from bellows chamber (162) through spill-over chamber (166), vent passage (164), fluid junction (158) and capillary channel (154), which, in turn, displaces and expels from inlet (156) the volume of cell-free plasma. In some embodiments of device (150) (e.g. where capillary channel (154) is straight), the angle (155) between capillary channel (154) and vent passage (164) is an acute angle. In some embodiments, such acute angle is selected to be within the range of from 0 to 45°.

As illustrated in FIGS. 4C and 4D, in either of the above embodiments, spill-over chamber (116) or (166) may be located in body (102) or (152), respectively, below passage (121) and (171), respectively. Or, in other words, respective spill-over chambers (116) and (166) may be disposed in body (102) or (152), respectively, downstream of passage (121) and (171), respectively, relative to the direction of centrifugal force (170). Such a configuration reduces the likelihood that blood entering the device could enter the bellows chamber.

One of ordinary skill in the art recognizes that the comments below referencing components of the embodiment of FIG. 1A are applicable to the corresponding components of the embodiment of FIG. 1B.

In some embodiments, bellows chamber (112) encloses a flat volume bound by two substantially parallel walls each having heights and widths of about the same magnitude and an inner-face separation of a smaller magnitude. At least one of the two walls includes vent port (118), typically but not necessarily disposed near the center of the wall, which (i) permits the venting of air from the interior of device (100) as the capillary channel fills with blood by capillary action and (ii) may be blocked or sealed manually by a finger or thumb when pressing the walls to expel plasma. In some embodiments, the shape, size and composition of the walls are suitable for receiving pressure by pressing, or pinching, the walls together by thumb and finger so that at least one wall is displaced by such pressure or pinching whereby the volume enclosed by bellows chamber (112) is reduced. In some embodiments, the walls are circular or substantially square or rectilinear encompassing an area in the range of about 1 to 8 cm$^2$; in other embodiments, the walls are circular or substantially square or rectilinear encompassing an area in the range of about 1 to 6 cm$^2$. In some embodiments, an inner-face separation may be in the range of from 1 to 10 mm.

Figure 2A:
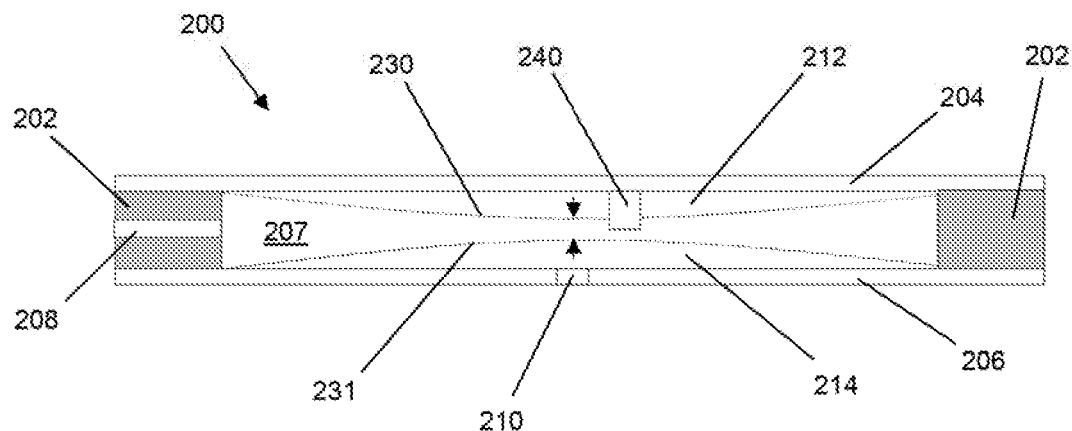
FIGS. 2A-2E illustrate the operation of bellows chambers of different embodiments of the invention.
Figure 2B:
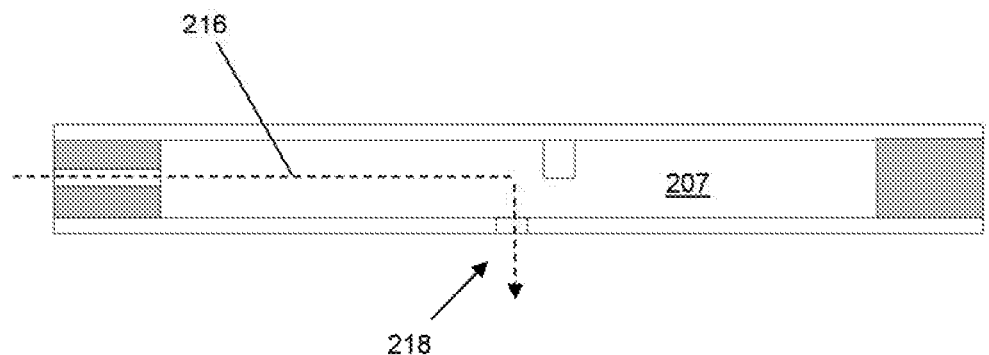
Figure 2C:
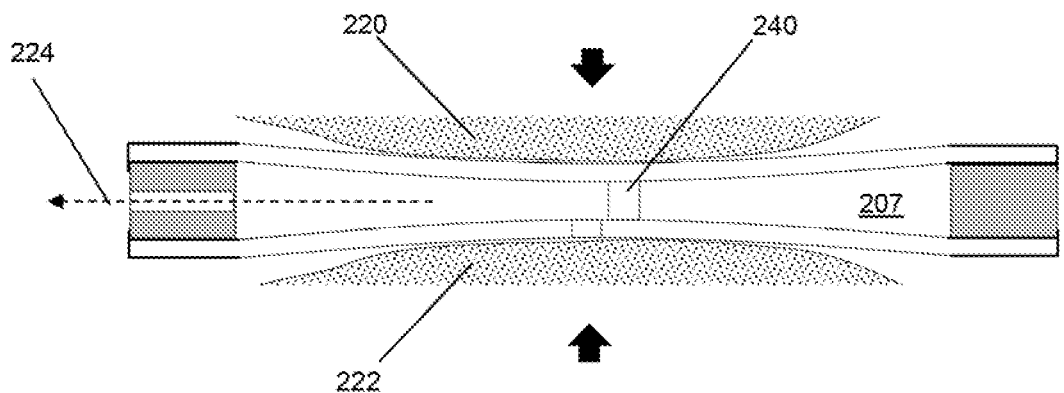

The function of the walls of one embodiment of bellows chamber (112) and its relationship to capillary channel (104) is illustrated in FIGS. 2A-2C which show cross sections of bellows chamber (200) during operation. In the illustrated embodiment, portions of body (202) are sealingly bonded to, and separate, sheets or covers (204) and (206) which, in turn, enclose volume (207) (that is, sheets or covers (204) and (206) serve as walls of bellows chamber (200)). Covers (204) and (206) comprise material and have thicknesses and flexibilities which permit them to be moved together manually so that volume (207) may be reduced, for example, as shown by dashed lines (230) and (231). Although both covers (204) and (206) are show in FIGS. 2A-2C as pliant or flexible upon pinching, in alternative embodiments only a single cover may be pliant or flexible for reducing the volume of bellows chamber (200). The difference between volume (207) in bellows chamber (112) in a resting state and volume (207) in a pinched state determines the amount of air (volumes 212 and 214) pushed out through vent passage (114) and capillary channel (104) (referred to herein interchangeably as the "expelled volume" or "bellows volume").

In some embodiments, the expelled volume may be regulated by including an optional stop (240) which limits how close covers (204) and (206) can be pressed together, thereby limiting the expelled volume to a maximum or predetermined amount, in some embodiments, a maximum expelled volume is substantially equal to the volume of the capillary channel, that is, the predetermined channel volume. In other embodiments, a maximum expelled volume is equal to or greater than the predetermined channel volume. In still other embodiments, a maximum expelled volume is in the range of 100 to 125 percent of the predetermined channel volume. Optional stop (240) also provides an indicator to a user of how much pressure to apply to covers (204) and (206); namely, apply manual pressure until resistance from stop (240) is encountered. That is, resistance from the stop would alert a user that an expelled volume has been generated. As illustrated by dashed line (216) in FIG. 2B, during, operation as blood enters the device and occupies the capillary channel, displaced air moves through vent passage (208) into bellows chamber (200) and is expelled (218) through vent port (210).

As illustrated in Fin. 2C, after a blood-loaded device is spun to remove red cells from the plasma in the capillary channel, a user may take the device between thumb (220) and index finger (222) (so that vent port (210) blocked) and pinch walls (204) and (206) together to drive an expelled volume of air out of bellows chamber (200), through vent passage (208), through the fluid junction and into the capillary channel, thereby expelling any plasma contained therein through and out of the input port.

Figure 2D:
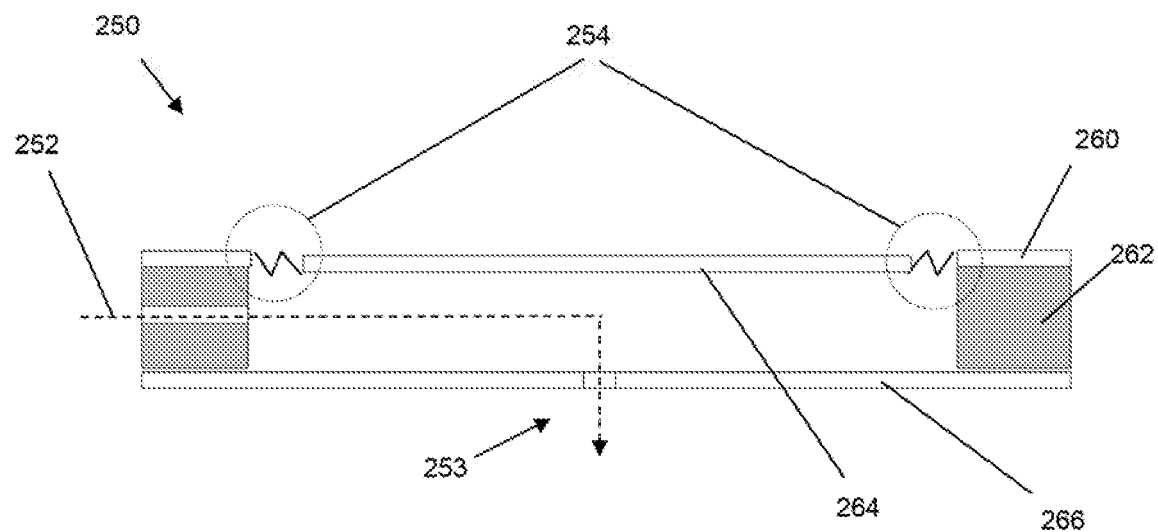
Figure 2E:
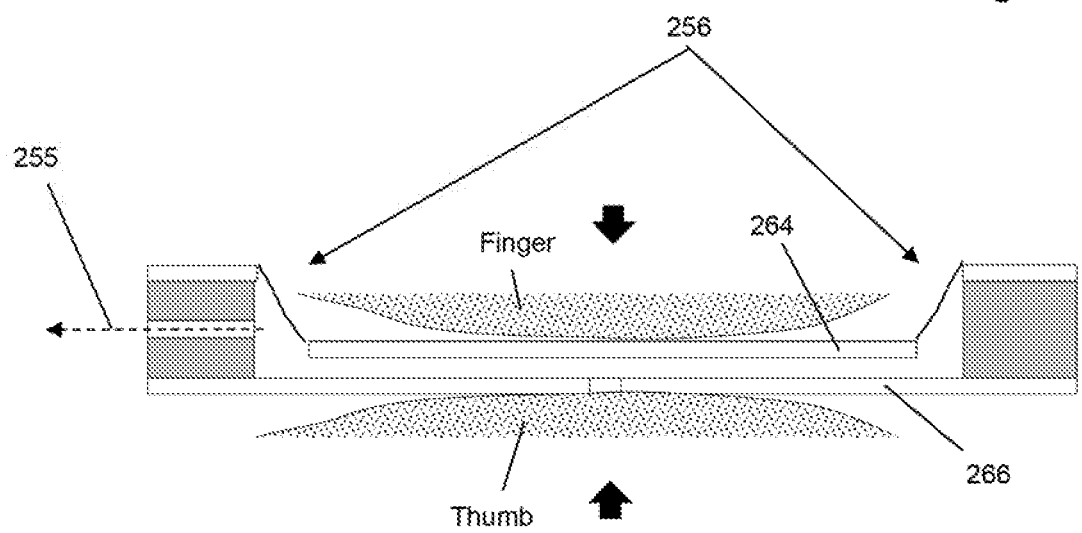
Figures 3A, 3B:
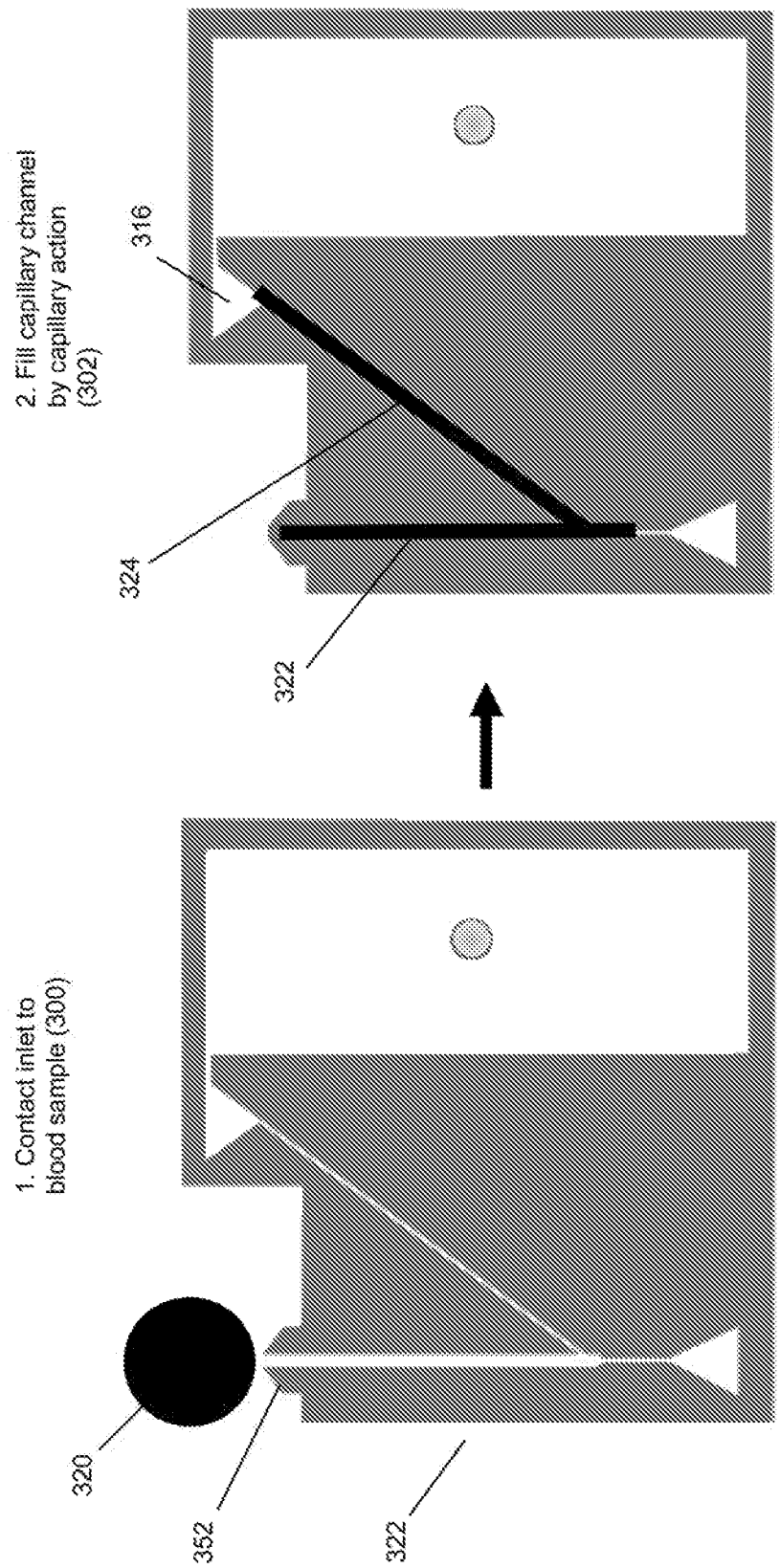

FIGS. 2D and 2E illustrate another embodiment of the invention comprising bellows chamber (250) that has a wall connected to cover (260) or body (262) by way of telescoping connection (254). Air (252) displaced by blood loaded into a capillary channel exits bellows chamber (250) through vent port (253) as in FIG. 2B. A known or predetermined volume of air (255) (i.e. an expelled volume) is then expelled through vent passage (257) when walls (264) and (266) are pinched together, thereby irreversibly extending telescoping connection (256) so that the volume of bellows chamber (250) is reduced by a fixed amount.

Figure 5:
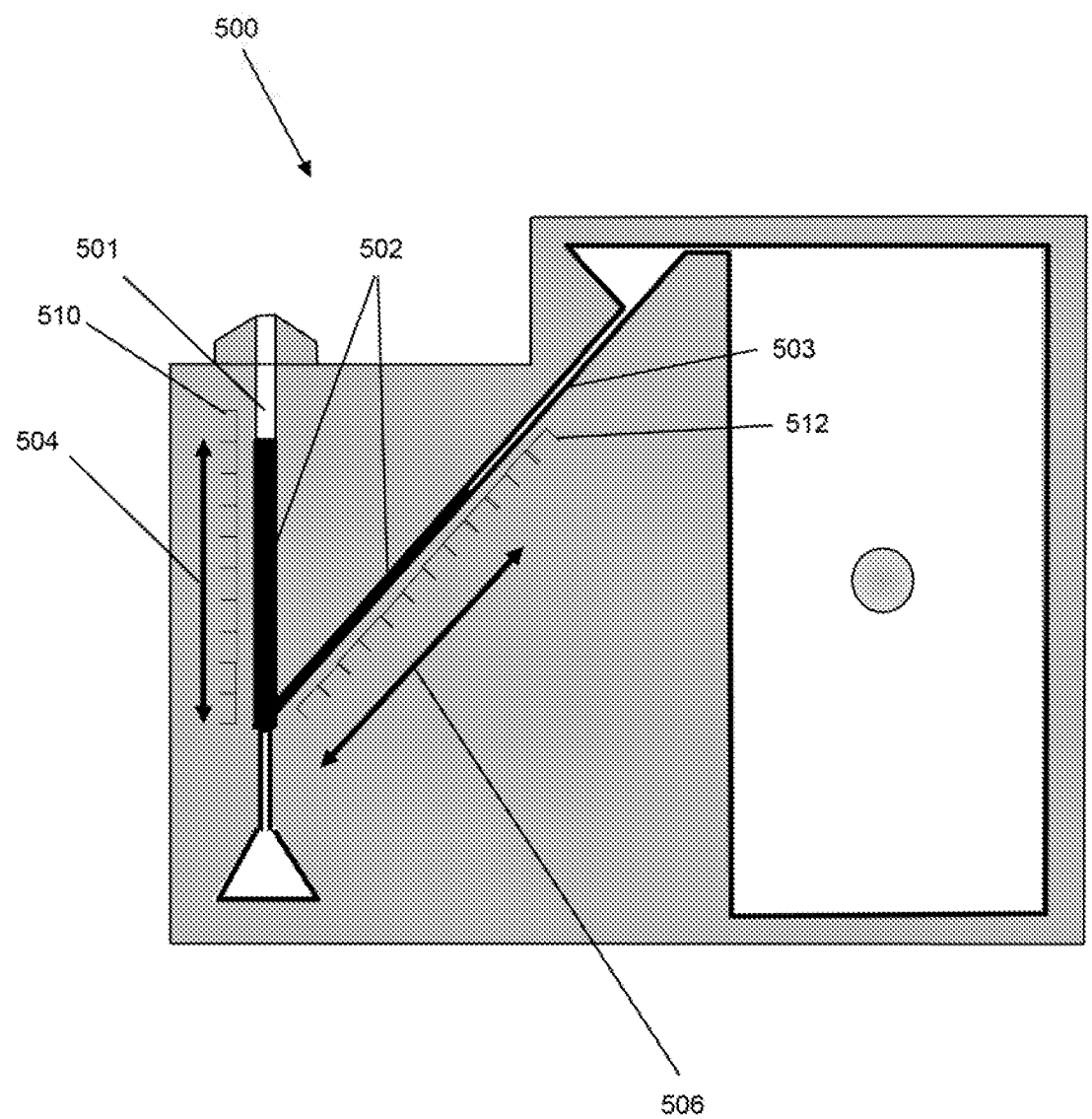
FIG. 5 illustrates another embodiment of the present invention which includes calibration marks adjacent to the capillary channel and vent passage fair convenient determination of blood and plasma sample volumes.

In some embodiments, as illustrated in FIG. 5, a device may include volume calibration markings along the capillary channel and vent passage to provide a precise measure of the volume of plasma that is expelled by the device. After centrifugation, plasma (502) may occupy space in capillary channel (501) and vent passage (503) as shown by the dark shading. Calibration scales (510) and (512) give measures of the volumes occupied in capillary channel (501) and (503), respectively. Volumes may be determined by visual inspection by comparing scale values with the extent of the plasma columns (504 and 506) in capillary channel (501) and vent passage (503), respectively. The volume determination may also be made automatically by an imaging device with conventional image processing capabilities.

In some embodiments, the volume and shape of capillary channel (104) or (154) is selected so that a volume of blood is taken up which provides a plasma sample with a volume in the range of from 1 to 200 uL after centrifugation and expelling the sample by operation of bellows chamber (112). In some embodiments, a volume of blood is taken up by capillary channel (104) which provides a plasma sample with a volume in the range of from 20 to 30 uL. By way of example, capillary channel (104) or (154) may be a 40 mm long tube with a diameter in the range of from 0.18 mm to 2.5 mm. In some embodiments, cell-holding chamber (110) or (160) has a volume with a magnitude of at least the volume of red blood cells in the blood sample taken up by device (100) or (150). In some embodiments, such a volume may be at least fifty percent of the volume of capillary channel (104) or (154); and in other embodiments, such a volume may be at least fifty-five percent of the volume of capillary channel (104) or (154). The shape of the cross section of the capillary channels in the various embodiments, e.g. (104) or (154), may vary and may be determined by the method of fabrication. In some embodiments, the shape of the cross section of the capillary channel is rectangular; in other embodiments, such shape may be circular; and in other embodiments, such shape may be trapezoidal or isosceles trapezoidal.

In some embodiments, the volumes of capillary channels (104) and (154), vent passages (114) and (164) and cell-holding chambers (110) and (160) may be configured to accommodate larger volumes of blood. For example, as illustrated in FIGS. 4C and 4D, in sonic embodiments such components may be configured to accommodate up to 500 uL, of blood, wherein capillary channels and vent passages have widths in the range of 3-4 mm, depths in the range of 3-6 mm.

Optional spill-over chamber (116) may be included as a safely feature to minimize the possibility that blood would enter bellows chamber (112) and possibly be released through vent port (118). The volume of spill-over chamber (116) may vary widely. In some embodiments, spill-over chamber (116) has a volume at least fifty-five percent of the volume of capillary channel (104).

Additionally and/or alternatively, bellows chamber (112) may contain or be filled with a porous foam or filter material that would block blood in vent passage (114) or spill-over chamber (116) from passing through bellows chamber (112) and through vent port (118) but that would not prevent compression of bellows chamber (112) to expel plasma after centrifugation. Alternatively or additionally, vent port (118) may include a one-way valve that allows air only to exit but not to enter into the bellows chamber through the port.

FIGS. 4A and 4B illustrate further embodiments of devices of the invention in which, passages and chambers have different geometries than those of the embodiments of FIGS. 1A and 1B. In particular, both the embodiments of FIG. 4A (device 400) and 4B (device 450) have circular cell-holding chambers (412) and spill-over chambers (422), whereas vent passage (416) of device (400) comprises two linear segments, one that runs parallel with the long axis of capillary channel (404) and one that connects with fluid junction (414) at an angle that may be in the range of 0 to 90 degrees. On the other hand, vent passage (452) of device (450) comprises a linear segment that runs parallel with the long axis of the capillary channel, but connects to fluid junction (454) by a curvilinear passage. FIG. 4A further gives illustrative dimensions of various chambers and passages. In some embodiments, diameter (406) of capillary passage (404) may be 2 mm; diameter (408) of vent passage (416) may be 0.5 mm: diameter (410) of the passage connecting fluid junction (414) to cell-holding chamber (412) may be 0.6 mm; width (420) of bellows chamber (418) may be 18 mm; and length (426) of bellows chamber (418) may be 31 mm.

FIGS. 4C and 4D illustrate further embodiments, including exemplary dimensions, of the devices of the invention wherein the spill-over chamber, vent passage, fluid junction, cell passage and cell-holding chamber are disposed linearly in the recited order. Device (460) in FIG. 4C has disposed in linear order spill-over chamber (468), vent passage (466), fluid junction (465), and cell-holding chamber (464). Where device (460) comprises a planar body, for example, 4.5 mm thick, the following components may have the following exemplary dimensions: capillary channel (462) may have length (463) of 20.91 mm and width (467) of 2.7 mm, vent passage (466) may have length (471) of 21.9 mm and width (472) of 2.7 mm, distance (473) between center of spill-over chamber (468) and top of bellows chamber (474) may be 4 mm, and radius (477) of cell-holding chamber (464) may be 8.5 mm. With such dimensions, device (460) has the capacity to take up about 500 uL of blood and cell-holding chamber has a volume of about 255 uL. Device (480) in FIG. 4D has disposed in linear order spill-over chamber (488), vent passage (485), fluid junction (485), and cell-holding chamber (484). Where device (480) comprises a planar body, for example 1 mm thick, the following components may have the following exemplary dimensions; capillary channel (482) may have length 24 mm and width of 1 mm (483), vent passage (486) may have length of 20 mm width (487) of 1 mm, and cell-holding chamber (484) may have diameter (489) of 5.2 mm. With such dimensions, device (480) has the capacity to take up about 45 uL, of blood and cell-holding chamber has a volume of about 21 uL.

Body (102) of device (100) may comprise, and the elements described above may be formed in, a wide variety of materials well-known in the microfluidics field, such as, silicon, glass, plastic, or the like. That is, devices of the invention may be fabricated as microfluidics devices using well-known techniques and methodologies of the microfluidic field. In some embodiments, body (102) comprises a plastic, such as, polystyrene, polyethylenetetraphthalate glycol, polyethylene terephthalate, polymethylmethacrylate, polyvinylchloride, polycarbonate, thermo plastic elastomer or the like. Devices of the invention may be fabricated with or in plastic using well-known techniques including, but not limited to, hot embossing, injection molding, laser cutting, milling, etching, 3D printing, or the like. Guidance in the selection of plastics and fabrication methodologies may be found in the following references: Becker et al, Talanta, 56: 257-287 (2002), Fiorini et al, Biotechniques, 38(3): 429-446 (2005); Bjornson et al, U.S. Pat. No. 6,803,019; Soane et al, U.S. Pat. No. 6,176,962; Schaevitz et al, U.S. Pat. No. 6,908,594; Neyer et al, U.S. Pat. No. 6,838,156; and the like, which references are incorporated herein by reference. In some embodiments, as illustrated in side view 1 of FIG. 1, body (102) may be sandwiched between, and bonded to, sheets (101) and (103), which may be made from the same or different materials and which may or may not be transparent. Such bonding may be accomplished in a varied of ways, including by way of adhesives, such as pressure sensitive adhesives. In other embodiments, as illustrated in side view 2 of FIG. 1, where chambers and passages are formed by hot embossing, body (102) may be covered with a single sheet (101). In either case, one or both sheets (101) and (103) may comprise the walls of bellows chamber (112).

In some embodiments, it may be desirable to modify the hydrophilicity of device surfaces in order to increase or decrease capillary action or to facilitate movement of fluids within a device. In particular, in some embodiments where plastic materials are employed, it may be desirable to treat surfaces to increase hydrophilicity to enhance capillary action. Such treatments may be carried out by a variety of techniques, including but not limited to, plasma treatment; exposure to reactive agents; adsorption of neutral or charged polymer, such as, polyethylene glycol, polysaccharides, polyacrylamide, polyvinylpyrrolidone; and the like.

The surface of the channels may be coated with various chemicals common to blood collection devices, such as anti coagulates including Sodium Heparin, EDTA, Sodium Citrate, Potassium Oxalate, Sodium Fluoride, etc., or other chemicals to induce aggregation of red-blood cells. Such at agents, or blood aggregants, include, but are not limited to, cross-linking antibodies, high molecular weight (HMW) polymers, beads, and the like. Exemplary HMW polymers include, hydroxyethyl starch, dextran, polyvinylpyrrolidone, poly-L-glutamic acid, and the like. In some embodiments, HMW polymers include 6% hydroxyethyl starch, 3% dextran (MW>73 kDa), polyvinylpyrrolidone (>360 kDa), poly-L-glutamic acid (>61 kDa), and the like. As mentioned above, the invention includes methods for generating a cell-free plasma sample using devices of the invention. In some embodiments, such methods comprise steps of (a) loading a sample of blood in a capillary channel by capillary action, wherein the capillary channel has a predetermined channel volume and dimensions and an inlet for accepting blood at a first end and a fluid junction at a second end, and wherein blood in excess of the predetermined channel volume enters a vent passage in fluid communication with the fluid junction; (b) centrifuging the capillary channel so that blood cells in the capillary channel and vent passage are sedimented in a cell-holding chamber downstream of and in fluid communication with the fluid junction by way of a cell passage, thereby leaving cell-free plasma in the capillary channel and vent passage; (c) expelling a volume of the cell-free plasma through the inlet of the capillary channel by manually compressing one or more pliant walls of a bellows chamber in fluid communication with the vent passage at an end opposite to that connected to the fluid junction, wherein the bellow chamber comprises two substantially parallel walls with at least one manually blockable vent port for exhausting air displaced during the loading step and wherein at least one wall is pliant by manual action so that the volume of the bellows chamber may be reduced by an amount substantially equal to the predetermined channel volume by manually pressing the two walls together. In some embodiments, a centrifugal force produced by the centrifuging step is directed along the long axis of the capillary channel and the capillary channel, fluid junction, cell passage and cell-holding chamber are linearly disposed in the indicated order so that cells in the blood sample are driven by the centrifugal force through the cell passage and into the chamber. As noted above, the cross-sectional dimensions of the cell passage are selected so that with no applied force (as in step (b)) cells do not enter, or tend not to enter, the cell passage. On the other hand, under centrifugal force cells of the blood sample in the capillary channel are readily forced through the cell passage and into the cell-holding chamber.

A further illustration of a method of operating of one embodiment of device of the invention is illustrated in FIGS. 3A-3D. In step 1 (300), inlet (352)) of device (350) is put into contact with blood sample (320), which may be a blood droplet from a pin prick, for example, in step 2 (302) capillary channel (322) fills by capillary action. Depending on the size, geometry and surface coatings or modifications, capillary action may cause blood to enter vent passage (324) or optional spill-over chamber (316). In step 3 (304), device (350) is spun so that centrifugal force (308) is exerted collinearly to axis (313) of capillary channel (322) in the direction of cell-holding chamber (328). Sufficient centrifugal force is applied so that blood cells, e.g. RBCs, sediment into cell-holding chamber (328). In step 4 (306), a user places the opposing walls of bellows chamber (335) between thumb (330) and index finger (not shown) and pinches them together, thereby driving, an expelled volume into capillary channel (322) from its end connected to fluid junction (354), thereby expelling plasma sample (332) through inlet (352).

The magnitude of centrifugal force applied to device (350) may vary depending on the embodiment, for example, depending on the geometry and dimension of channels and chamber, whether all cells or just red blood cells are separated from plasma, or like factors. In one embodiment, a centrifugal force may be applied using a conventional benchtop laboratory centrifuge, e.g. with 10 cm diameter rotor, operating at 5000 rpm for 1-2 min, or the equivalent thereof. In other embodiments, a wide variety of other devices may be used to generate a centrifugal force for separating blood cells from plasma in the device of the invention, including but not limited to, mechanical hand operated centrifuges, low-power CD-based drives, or the like, e.g. such as disclosed in the following references, which are incorporated by reference, Madou et al, Ann. Rev. Biomed. Eng., 8: 601-628 (2006): Smith et al, Micromachines, 7(22): mi7020022 (2016); Wong et al, LabChip, 8: 2031-2037; (2008); or the like.

While the present invention has been described with reference to several particular example embodiments, those skilled in the art will recognize that many changes may be made thereto without departing from the spirit, and scope of the present invention. The present invention is applicable to a variety of sensor implementations and other subject matter, in addition to those discussed above.

Kits

The invention includes kits for carrying out methods of the invention. In some embodiments, a kit of the invention comprises a device of the invention. In other embodiments, a kit comprises one or more devices of the invention along with instructions for using the device. In some embodiments, kits of the invention comprise one or more devices of the invention and one or more devices for generating a centrifugal force in accordance with methods of the invention. Devices for generating a centrifugal force may include hand operated devices or battery operated devices, such as compact disc player drives or hard disc drives adapted to hold in proper orientation blood separation devices of the invention.

Definitions

"Microfluidics" device or "nanofluidics" device, used interchangeably herein, each means an integrated system for capturing, moving, mixing, dispensing or analyzing small volumes of fluid, including samples (which, in turn, may contain or comprise cellular or molecular analytes of interest), reagents, diluents, buffers, or the like. Generally, reference to "microfluidics" and "nanofluidics" denotes different scales in the size of devices and volumes of fluids handled. In some embodiments, features of a microfluidic device have cross-sectional dimensions of less than a few hundred square micrometers and have passages, or channels, with capillary dimensions, e.g. having maximal cross-sectional dimensions of from about 500 μm to about 0.1 μm. In some embodiments, microfluidics devices have volume capacities in the range of from 1 μL to a few nL, e.g. 10-100 nL. Dimensions of corresponding features, or structures, nanofluidics devices are typically from 1 to 3 orders of magnitude less than those for microfluidics devices. One skilled in the art would know from the circumstances of a particular application which dimensionality would be pertinent. In some embodiments, microfluidic or nanofluidic devices have one or more chambers, ports, and channels that are interconnected and in fluid communication and that are designed for carrying out one or more analytical reactions or processes, either alone or in cooperation with an appliance or instrument that provides support functions, such as sample introduction, fluid and/or reagent driving means, such as positive or negative pressure, acoustical energy, or the like, temperature control, detection systems, data collection and/or integration systems, and the like. In some embodiments, microfluidics and nanofluidics devices may further include valves, pumps, filters and specialized functional coatings on interior walls, e.g. to prevent adsorption of sample components or reactants, facilitate reagent movement by electroosmosis, or the like. Such devices may be fabricated as an integrated device in a solid substrate, which may be glass, plastic, or other solid polymeric materials, and may have a planar format for ease of detecting and monitoring sample and reagent movement, especially via optical or electrochemical methods. In some embodiments, such devices are disposable after a single use. In some embodiments, microfluidic and nanofluidic devices include devices that form and control the movement, mixing, dispensing and analysis of droplets, such as, aqueous droplets immersed in an immiscible fluid, such as a light oil. The fabrication and operation of microfluidics and nanofluidics devices are well-known in the art as exemplified by the following references that are incorporated by reference: Ramsey, U.S. Pat. Nos. 6,001,229; 5,858,195; 6,010,607; and 6,033,546; Soane et al, U.S. Pat. Nos. 5,126,022 and 6,054,034; Nelson et al, U.S. Pat. No. 6,613,525; Maher et al, U.S. Pat. No. 6,399,952; Ricco et al, International patent publication WO 02/24322; Bjornson et al, international patent publication WO 99/19717; Wilding et al, U.S. Pat. Nos. 5,587,128; 5,498,392; Sia et al, Electrophoresis, 24: 3563-3576 (2003); Unger et al, Science, 288: 113-116 (2000); Enzelberger et al, U.S. Pat. No. 6,960,437; Cao, "Nanostructures & Nanomaterials: Synthesis, Properties & Applications," (Imperial College Press, London, 2004); Haeberle et al. LabChip, 7: 1094-1110 (2007); Cheng et al, Biochip Technology (CRC Press, 2001); and the like.

What is claimed is:

1. A device for separating plasma from whole blood, the device comprising:
    a body comprising a capillary channel having a predetermined channel volume and dimensions and having an inlet at a first end and a fluid junction at a second end;
    a cell-holding chamber disposed opposite the fluid junction from the capillary channel in the body, the cell-holding chamber being in fluid communication with the fluid junction by a cell passage;
    a single bellows chamber disposed in the body, the bellows chamber providing a predetermined bellows volume enclosed by two substantially parallel walls wherein at least one wall contains a manually blockable vent port therethrough and wherein at least one wall is compressed by manual action of a user to a bellows stop or is compressed by manual action of a user to irreversibly extend a telescoping connection thereof so that the predetermined bellows volume is reduced by an amount substantially equal to the predetermined channel volume;
    a vent passage disposed in the body providing fluid communication between the fluid junction and the bellows chamber so that a volume of air may be forced into the vent passage from the bellows chamber by manually pressing the two substantially parallel walls together; and
    wherein the device is configured so that (i) the predetermined channel volume and dimensions permit the capillary channel to fill with blood by capillary action upon contact therewith at the inlet, (ii) blood cells in the capillary channel and vent passage sediment in the cell-holding chamber by centrifugation so that only substantially cell-free plasma remains in the capillary channel and vent passage, and (iii) substantially cell-free plasma in the capillary channel and vent passage is expelled from the inlet by manually covering the vent port by the user and pressing the walls of the bellows chamber together, thereby forcing air from the bellows chamber, through the vent passage, and into the capillary channel to expel the plasma.

2. The device of claim 1 wherein said capillary channel has a long axis and wherein said cell-holding chamber is disposed opposite said fluid junction from said capillary channel along the long axis of said capillary channel.

3. The device of claim 1 wherein said vent passage is disposed in said body at an acute angle with respect to a long axis of said capillary channel.

4. The device of claim 1 wherein said body is composed of glass, silicon or plastic.

5. The device of claim 4 wherein said body is composed of plastic.

6. The device of claim 5 wherein said plastic is polystyrene, polyethylenetetraphthalate glycol, polymethylmethacrylate, polyethylene terephthalate, polyvinylchloride, or polycarbonate.

7. The device of claim 1 wherein said capillary channel has a diameter in the range of 0.18 mm to 3 mm.

8. The device of claim 7 wherein said capillary channel has a length in the range of from 20 to 50 mm.

9. The device of claim 1 wherein said predetermined channel volume is in the range of from 1 µL to 500 µL.

10. The device of claim 1 wherein said cell-holding chamber has a volume at least one half of said channel volume.

11. The device of claim 1 wherein said vent passage has a long axis and wherein said cell-holding chamber is disposed opposite said fluid junction from said vent passage along the long axis of said vent passage and wherein said cell passage connecting said cell-holding chamber with said fluid junction has a long axis that is collinear with the long axis of said vent passage.

12. The device of claim 11 wherein said capillary channel is disposed in said body at a substantially acute angle with respect to said long axis of said vent passage.

13. The device of claim 12 wherein said body is composed of glass, silicon or plastic.

14. The device of claim 13 wherein said body is composed of plastic.

15. The device of claim 1 further comprising a spill-over chamber disposed in said body between, and in fluid communication with, said vent passage and said bellows chamber, the spill-over chamber accepting excess blood from said capillary channel and vent passage so that said bellows chamber remains free of blood upon capillary filling of said device.

16. The device of claim 1 wherein blood cells are red blood cells.

17. A method for separating plasma from whole blood, the method comprising:
    loading a sample of blood in a capillary channel by capillary action, wherein the capillary channel has a predetermined channel volume and dimensions and has an inlet at a first end and a fluid junction at a second end, and wherein blood in excess of the predetermined channel volume enters a vent passage in fluid communication with the fluid junction;

centrifuging the capillary channel so that blood cells in the capillary channel and vent passage are sedimented in a cell-holding chamber downstream of and in fluid communication with the fluid junction by a cell passage, thereby leaving substantially cell-free plasma in the capillary channel and vent passage;

expelling a predetermined volume of the substantially cell-free plasma through the inlet of the capillary channel by a single manual compression of one or more pliant walls of a bellows chamber in fluid communication with the vent passage, wherein the bellows chamber comprises two substantially parallel walls wherein at least one of said walls comprises a manually blockable vent port for exhausting air displaced during the loading step and wherein at least one wall is pliant by manual action so that the blockable vent port is blocked and a volume of air in the bellows chamber substantially equal to the predetermined channel volume is forced through the vent passage and into the capillary channel by manually pressing the two walls together thereby expelling the predetermined volume of substantially cell-free plasma.

18. The method of claim 17 wherein said volume of air expelled from said bellows chamber into said vent passage is substantially equal to said predetermined channel volume.

19. The method of claim 17 wherein said capillary channel, said fluid junction, said cell passage, said cell-holding chamber, said vent passage and said bellows chamber are integrated and interconnected in a single plastic body.

20. The method of claim 19 wherein said vent passage, said fluid junction, said cell passage and said cell-holding chamber are disposed linearly in said plastic body so that during said centrifugation step a centrifugal force is applied collinearly with such disposition and said blood cells from said vent passage pass through said fluid junction and said cell passage and sediment in said cell-holding chamber.

21. The method of claim 17 wherein during said centrifugation step air in said cell-holding chamber is displaced by blood cells and escapes therefrom by moving through said cell passage, said fluid junction and said vent passage.

* * * * *